(12) United States Patent
Horton et al.

(10) Patent No.: US 9,210,930 B2
(45) Date of Patent: *Dec. 15, 2015

(54) CONTROL OF SUBMERGED AQUATIC VEGETATION

(75) Inventors: Christopher Todd Horton, Anderson, SC (US); Joseph G. Vollmer, Laramie, WY (US); James Crosby, Georgetown, TX (US)

(73) Assignee: BASF SE, Ludwigshafen (DE)

( * ) Notice: Subject to any disclaimer, the term of this patent is extended or adjusted under 35 U.S.C. 154(b) by 705 days.

This patent is subject to a terminal disclaimer.

(21) Appl. No.: 12/425,126

(22) Filed: Apr. 16, 2009

(65) Prior Publication Data

US 2010/0093540 A1  Apr. 15, 2010

Related U.S. Application Data

(63) Continuation-in-part of application No. 12/158,227, filed as application No. PCT/EP2006/070009 on Dec. 20, 2006, now Pat. No. 9,060,516.

(60) Provisional application No. 60/752,906, filed on Dec. 23, 2005, provisional application No. 60/802,791, filed on May 24, 2006, provisional application No. 61/045,689, filed on Apr. 17, 2008.

(51) Int. Cl.
  *A01N 47/10* (2006.01)
  *A01N 43/42* (2006.01)
  *A01N 43/40* (2006.01)

(52) U.S. Cl.
  CPC ............. *A01N 43/42* (2013.01); *A01N 43/40* (2013.01)

(58) Field of Classification Search
  CPC ............................... A01N 43/42; A01N 43/40
  See application file for complete search history.

(56) References Cited

U.S. PATENT DOCUMENTS

| | | | |
|---|---|---|---|
| 4,398,937 A * | 8/1983 | van Aller et al. | 504/157 |
| 4,497,651 A | 2/1985 | Hagen et al. | |
| 4,632,696 A | 12/1986 | Hagen et al. | |
| 4,715,889 A | 12/1987 | Hagen et al. | |
| 4,798,619 A | 1/1989 | Los | |
| 5,334,576 A | 8/1994 | Doehner, Jr. et al. | |
| 5,973,154 A | 10/1999 | Drabb et al. | |
| 6,339,158 B1 | 1/2002 | Wepplo et al. | |
| 6,677,276 B1 * | 1/2004 | Hacker et al. | 504/127 |
| 2002/0119891 A1 | 8/2002 | Netherland | |
| 2003/0186815 A1 * | 10/2003 | Hacker et al. | 504/127 |
| 2008/0305954 A1 | 12/2008 | Zawieruba et al. | |
| 2009/0011934 A1 * | 1/2009 | Zawieruba et al. | 504/128 |
| 2010/0093540 A1 * | 4/2010 | Horton et al. | 504/130 |

FOREIGN PATENT DOCUMENTS

| | | |
|---|---|---|
| CN | 1401232 | 3/2003 |
| EP | 0 094 181 | 11/1983 |
| EP | 0 127 433 | 12/1984 |
| WO | WO 2005/077169 | 8/2005 |
| WO | WO 2005/096814 | 10/2005 |
| WO | WO 2007/014758 | 2/2007 |
| WO | WO 2007/014760 | 2/2007 |
| WO | WO 2007/014761 | 2/2007 |
| WO | WO 2007/042447 | 4/2007 |
| WO | WO 2007/071655 | 6/2007 |

OTHER PUBLICATIONS

Capers et al. (Invasive Aquatic Plants, Connecticut Agricultural Experiment Station, Bulletin No. 997, Jan. 2005).*
Michel et al. (Somatic mutation-mediated evolution of herbicide resistance in the nonindigenous invasive plant hydrilla, Molecular Ecology, vol. 13, 2004, p. 3229-3237).*
Tanaka et al. (Evaluation of herbicides for the control of egeria laboratory water box and dam without water flow, Plant Weed vol. 20, p. 73-81, 2002).*
Hoyer, M.V., et al. "Hydrilla Management in Florida: A Summary and Discussion of Issues Identified by Professionals with Future Management Recommendations" [online] University of Florida Department of Fisheries and Aquatic Sciences, Jun. 2005.
Nelson, Linda, et al. "Response of Wild Rice to Selected Aquatic Herbicides", U.S. Army Corps of Engineers, Sep. 2003.

(Continued)

*Primary Examiner* — Rebecca Prouty
*Assistant Examiner* — Danielle Sullivan
(74) *Attorney, Agent, or Firm* — Brinks Gilson & Lione

(57) ABSTRACT

A method for controlling aquatic weeds which comprises applying a herbicidally effective amount of a solid formulation of at least one compound of formula (I)

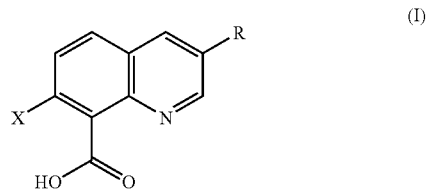

wherein
  X is halogen and
  R is halogen or $C_1$-$C_6$ alkyl,
and/or one or more agriculturally acceptable salts thereof to the bottom of the aqueous habitat of the aquatic weeds to act on submersed aquatic weeds and/or their aqueous habitat containing seeds or other propagating organs of said aquatic weeds.

18 Claims, No Drawings

(56) References Cited

OTHER PUBLICATIONS

Anderson, L.W.J, "A review of aquatic weed biology and management research conducted by the United States Department of Agriculture—Agricultural Research Services", Pest Manag. Sci., 2003, pp. 801-813, vol. 59.

Anderson, Lars, W.J., "Movement of 14-C Arsenal® (imazapyr) into monoecious Hydrilla verticillata tubers", Res Prog. Rep. West. Soc. Weed Sci, 1986 Meeting, p. 304.

Arias, Renee S., et al., "Molecular evolution of herbicides resistance to phytoene desaturase inhibitors in *Hydrilla verticillata* and its potential use to generate herbicide-resistant crops" Pest Manag Sci, 2005, p. 258-268, vol. 61.

Beck, J., et al., "Quinclorac (BAS 514) and its Herbicide-Combinations in Transplanted Rice in Japan" Proc. 12th Conf. of Asia-Pacific Weed Science Society, 1989, p. 235-244.

Braverman, M.P. et al., "Weed Control in Rice (*Oryza sativa*) with Quinclorac and Bensulfuron Coating of Granular Herbicides and Fertilizer" Weed Technology, 1995, p. 494-498, vol. 9.

Database CA [Online] Chemical Abstracts Service, Columbus, Ohio, US; XP002464636 retrieved from STN-International Database accession No. 141:84041, Jul. 29, 2004.

Gallagher, J. et al., "History and Development of Aquatic Weed Control in the United States", Rev. Weed Sci, 1990, p. 115-195, vol. 5.

Grossman, Klaus, "Quinclorac belongs to a new class of highly selective auxin herbicides", Weed Science, 1998, p. 707-716, vol. 46.

Netherland, M.D., et al., "Aquatic Plant Management: Invasive species and Chemical Control", Outlooks on Pest Management (Pesticide Outlook), Jun. 2005, pp. 100-104, vol. 16, No. 3.

Kay, S. H., et al., "Response of Two Alligatorweed Biotypes to Quinclorac" Journal of Aquatic Plant Management, Society, Washington, DC US , 1992, pp. 35-40, vol. 30, XP008086947 ISSN: 0146-6623.

Klingman, et al., "Aquatic-Weed Control" Weed Science, Weed Science Society of America, Champaign, II, US, 1982, pp. 383-402, XP002962279 ISSN: 0043-1745, p. 389: tables 29-1.

Langeland, K., et al. "Efficacy of Herbicide Active Ingredients Against Aquatic Weeds". Biology and Control of Algae. Agronomy Department Document SS AGR 44, Florida Cooperative Extension Service, Institute of Food and Agricultural Sciences, University of Florida, Gainesville, FL 32611, Sep. 2006, http://www.edis.ifas.ufl.edu/.

Mabbayad, M.O., et al., "Herbicide seed treatment for weed control in wet-seeded rice", Tropical Pest Management, 1992, p. 9-12, vol. 38, No. 1.

Street, J.E., et al., "Rice (*Oryza sativa*) Weed Control With Soil Applications of Quinclorac" Weed Technology, 1993, p. 600-604, vol. 7.

"The e-Pesticide Manual (Thirteenth Edition) Version 3.0" 2003, British Crop Protection Council , XP002464632 entry 712: "Quinclorac".

"The e-Pesticide Manual (Thirteenth Edition) Version 3.0" 2003, British Crop Protection Council , XP002464633 entry 713: "Quinmerac".

"The e-Pesticide Manual (Thirteenth Edition) Version 3.0" 2003, British Crop Protection Council , XP002464634 entry 211: "2,4-D".

Zoschke, A., et al., "CGA142'464 plus BAS-514, a new timing-flexible herbicide combination for broadspectrum weed control in rice (*Oryza sativa* L.) in South Korea", 12th Asian-Pacific Weed Science Society Conference, 1989, pp. 245-253, No. 1. and XP002464635 retrieved from STN-International Database accession No. 91:73631.

Rattray, M.R., et al., "The Mechanism of Action of Bensulfuron-Methyl on Hydrilla", J. Aquatic Plant Manage., 1993, p. 39-42, vol. 31.

\* cited by examiner

CONTROL OF SUBMERGED AQUATIC VEGETATION

CROSS REFERENCE TO RELATED APPLICATIONS

This application is a continuation-in-part of U.S. application Ser. No. 12/158,227 now U.S. Pat. No. 9,060,516, which is the National Stage application of International Application No. PCT/EP2006/070009, filed Dec. 20, 2006, which claims the benefit of U.S. Provisional Application Nos. 60/752,906 and 60/802,791, filed Dec. 23, 2005 and May 24, 2006, respectively; the entire contents of all of the aforementioned applications are hereby incorporated herein by reference. This application also claims the benefit of U.S. Provisional Application No. 61/045,689, filed Apr. 17, 2008; the entire contents of which are hereby incorporated herein by reference.

BACKGROUND

The invention belongs to the field of agricultural chemistry and provides to the art a method for controlling aquatic weeds. Such weeds clog waterways, plug up waterhandling equipment, and are often aesthetically unacceptable. They are cumbersome for fisherman, swimmers, and watersports. The economic impact for control and management in general and on recreational areas in particular is estimated to be in the millions of dollars.

A typical representative for inventively controlled aquatic weeds is *hydrilla* that is known as a submersed, very prolific, mat forming species, which can dominate the aquatic system that it is present in. High densities of *hydrilla* interfere with various water uses.

A typical representative is *Hydrilla verticillata*.

Therefore, the development of methods for controlling aquatic weeds, in particular *hydrilla*, is important.

Generally, aquatic weeds and herbicidal or biological methods for controlling them are known, for example from L. W. J. Anderson, Pest Manag. Sci. 59, pages 801-813 (online 2003) or M. D. Netherland et al., Outlooks on Pest Management (Pesticide Outlook), pages 100-104 or J. Gallagher and W. T. Haller, Rev. Weed Sci., 1990, 5, 115-192.

Herbicides that are used for controlling aquatic weeds should fulfil one or more of the following requirements.

The compounds must be effective and efficient.

They should not be harmful to other plants than the ones to be controlled, to animals and man.

They are preferably degradable within a reasonable timeframe and the degradation products are harmless as well.

It is desirable that the compositions comprising the compounds used to control aquatic weeds have a slow activity and, therefore, less oxygen-depleting for the water. On the other hand, it may also be desirable that the compositions have a high activity which allows to eliminate fast-growing aquatic weeds in a short timeframe.

Langeland et al., "Effficacy of Herbicide Active Ingredients Against Aquatic Weeds" September (2006), University of Florida, indicates that 2,4-D and Triclopyr are not recommended for control of *hydrilla*. Klingman et al., "Aquatic-Weed Control", Weed Science Society of America, Champaign, Ill., US (1982), pages 383-402 also shows in Table 29-1 that 2,4-D does not provide for control of *hydrilla*.

WO 2007/071730 discloses that chinolin herbicides, like quinclorac and quinmerac, provide growth suppression or control of submersed aquatic weeds in general and of *hydrilla* in particular. Application methods disclosed in this document aim at a uniform dilution of the active ingredient in the water body.

According to this document, the herbicides are applied to the water column in liquid or solid formulations. Even though the disclosed herbicides are very effective, there is still room for improvement regarding the control of specific aquatic weeds or specific conditions.

SUMMARY

It has now been found that the efficacy of quinclorac and related herbicides can be considerably improved by using a specific application technique.

The invention therefore provides a method for the control of aquatic weeds which comprises applying a herbicidally effective amount of a solid formulation of at least one compound of formula (I)

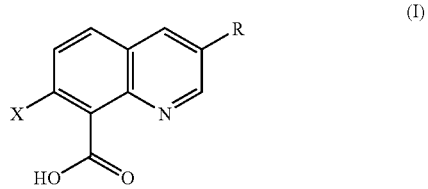

(I)

wherein
X is halogen and
R is halogen or $C_1$-$C_6$ alkyl,
and/or one or more agriculturally acceptable salts thereof to the bottom of the aqueous habitat of the aquatic weeds to act on submersed, preferably bottom rooted, aquatic weeds and/or their aqueous habitat containing seeds or other propagating organs of said aquatic weeds.

In a further aspect of the invention there is provided the use of a solid formulation composition comprising a herbicidally effective amount of a compound of formula (I) for controlling submersed aquatic weeds by application of the solid formulation to the bottom of the aqueous habitat of the aquatic weeds.

DETAILED DESCRIPTION

Chinoline derivatives in general, and 3,7-dichloroquinoline-8-carboxylic acid (quinclorac) and 7-chloro-3-methylquinoline-8-carboxylic acid (quinmerac) in particular, are known herbicides, which are described for example in U.S. Pat. No. 4,497,651, U.S. Pat. No. 4,632,696 and U.S. Pat. No. 4,715,889.

Quinclorac is a known herbicide to be used for the protection of grains in general and of rice in particular. The control of weeds in rice is described in a number of publications.

J. Beck, M. Ito, S. Kashibuchi, *Quinclorac (BAS 514) and its Herbicide-Combinations in Transplanted Rice in Japan in: Proc.* 12*th Conf. of Asia-Pacific Weed Science Society,* 1989, 235-244 describe the control of several weeds which are typically present in paddy rice such as *Echinachloa crusgalli, Cyperus difformis* or *Monochoria vaginalis* by means of quinclorac either as a single herbicide or in combination with several other herbicides.

In J. E. Street, T. C. Mueller, Rice (*Oryza sativa*) Weed Control With Soil Applications of Quinclorac in: *Weed Technology,* 1993, 7, 600-604 the control of troublesome weeds with regard to rice growth by application to dry or wet soil is described. The weeds under regard have been barnyardgrass (*Echinachloa crus-galli*), pitted morningglory (*Ipomoea lacunose*) and hemp sesbania (*Sesbania exaltata*).

The control of a mixture of different weeds in rice by means of e.g. quinclorac or quinclorac and bensulfuron is described by M. O. Mabbayad, K. Moody, *Herbicide seed treatment for weed control in wet-seeded rice in: Tropical Pest Management*, 1992, 38(1), 9-12.

The coating of different kinds of granules with quinclorac is described in M. P. Braverman, *Weed Control in Rice (Oryza sativa) with Quinclorac and Bensulfuron Coating of Granular Herbicides and Fertilizer in: Weed Technology*, 1995, 9, 494-498. The weeds under regard have been ducksalad (*Heteranthera limosa*) and junglerice (*Echinachloa colona*).

A weed generally is an unwanted plant. A plant is described as unwanted if its presence is not wanted in a particular place.

Aquatic weeds are unwanted plants that have adapted to living in or on aquatic environments. This includes water as well as water-saturated soil. Thus, their habitat means the living space of the plants including but not limited to water environment like sweet water or salt water sources, either as moving water or still water. Examples thereof are lakes, rivers, streams, wetlands, ponds, creeks, swamps, canals, reservoirs, and ditches. Other examples are marine water environments like oceans, seas, gulfs, and straits. Examples of saturated soils are water-saturated fields, in particular paddy fields.

Aquatic weeds can be further distinguished.

"Emersed aquatic weeds" grow standing out of the water or in water-saturated soil. A typical representative for an emersed species is alligatorweed (*Alternanthera philoxeroides*). Further examples are cattails, bulrushes, and purple loosestrife.

"Submersed aquatic weeds" grow with all or most of their vegetative tissue below the water surface. Typical representatives for submersed species are *hydrilla* (*Hydrilla*) and milfoil (*Myriophyllum*). Further examples include coontail, sego pondweed, southern naiad, *Egeria*, and *Potamogetun* species.

"Floating aquatic weeds" float on the water surface. Examples are duckweeds, waterhyacinth, water-lettuce, water-fens, and water-lilies.

"Algae" are considered 'primitive' plants but are often incorporated into the generic group of aquatic weeds.

"Controlling of submersed aquatic weeds" means that at least one submersed aquatic weed is controlled.

As used herein, the term "beneficial aquatic plants" means *sagittaria*, pickerelweed, *eleocharis*, knotgrass, and maidencane.

The term "controlling" in this context means exhibiting aquatic-herbicidal action. This means that the growth of at least one aquatic weed species is reduced or suppressed concerning number and/or size of its plants yielding in e.g. limited growth or death of the weeds.

The symbols in formula (I) are further illustrated in the following.

Halogen denotes fluorine, chlorine, bromine or iodine.

The alkyl moiety mentioned in the definition of radical R and possible salts is a collective term for individual enumerations of the individual group members. The hydrocarbon chain may be straight-chain or branched.

Examples for such meanings are:
$C_1$-$C_4$-alkyl: for example: methyl, ethyl, n-propyl, 1-methylethyl, n-butyl, 1-methylpropyl, 2-methylpropyl and 1,1-dimethylethyl;
$C_1$-$C_6$-alkyl: $C_1$-$C_4$-alkyl as mentioned above and also, for example: n-pentyl, 1-methyl-butyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl.

The alkoxy moiety mentioned in the definition of possible salts is a collective term for individual enumerations of the individual group members. The hydrocarbon chain may be straight-chain or branched.

Examples for such meanings are:
$C_1$-$C_4$-alkoxy: for example: methoxy, ethoxy, n-propoxy, 1-methylethoxy, n-butoxy, 1-methylpropoxy, 2-methylpropoxy and 1,1-dimethylethoxy;
$C_1$-$C_6$-alkoxy: $C_1$-$C_4$-alkoxy as mentioned above and also, for example: n-pentoxy, 1-methyl-butoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1-ethyl-1-methylpropoxy and 1-ethyl-3-methylpropoxy.

In a preferred embodiment of the invention X in compound of formula (I) is chlorine.

In a further preferred embodiment R in compound of formula (I) is chlorine or $C_1$ to $C_4$ alkyl.

Particularly preferred R in compound of formula (I) is chlorine or methyl, especially preferred R is chlorine, also especially preferred R is methyl.

Particularly preferred are the compounds where X is chlorine and R is chlorine (quinclorac) and where X is chlorine and R is methyl (quinmerac). Quinclorac is especially preferred. Further, quinmerac is especially preferred. Compounds having a half life in a body of water of about 50-60 days in water are preferred.

The method according to the invention may comprise
(Ia) one or more compounds of formula (I) in the form of the free carboxylic acid or
(Ib) one or more agriculturally acceptable salts of compounds of formula (I) or
(Ic) mixtures comprising two or more compounds chosen from (Ia) and (Ib).

In general, those salts of compounds of formula (I) are suitable, wherein the acidic hydrogen of the carboxylic group is substituted by a cation and the cation has no adverse effect on the action of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, di(2-hydroxyeth-1-yl) ammonium, benzyltrimethylammonium, benzyltriethylammonium, furthermore phosphonium ions, sulfonium ions, preferably tri($C_1$-$C_4$alkyl)sulfonium such as trimethylsulfonium, and sulfoxonium ions, preferably tri($C_1$-$C_4$-alkyl)sulfoxonium.

Another particularly preferred embodiment of the invention comprises a method of using of compound of formula (I) for controlling submersed aquatic weeds wherein the aquatic weeds are tolerant and/or resistant to the herbicide fluridone.

Compounds of formula (I) and/or one or more agriculturally acceptable salts thereof can be used in combination with one or more other herbicide(s) or an agriculturally acceptable salt or derivative thereof.

In the following compounds of formula (I) and/or one or more agriculturally acceptable salts thereof and, where applicable, one or more other herbicide(s) or an agriculturally acceptable salt or derivative thereof will be designated as active compounds.

Examples of such other herbicide(s) are the herbicides (a) selected from the following classes a1) to a15):
a1) lipid biosynthesis inhibitors;
a2) acetolactate synthase inhibitors (ALS inhibitors);
a3) photosynthesis inhibitors;
a4) protoporphyrinogen-IX oxidase inhibitors;
a5) bleacher herbicides;
a6) enolpyruvyl shikimate 3-phosphate synthase inhibitors (EPSP inhibitors);
a7) glutamine synthetase inhibitors;
a8) 7,8-dihydropteroate synthase inhibitors (DHP inhibitors);
a9) mitose inhibitors;
a10) inhibitors of the synthesis of long chain fatty acids (VLCFA inhibitors);
a11) cellulose biosynthesis inhibitors;
a12) decoupler herbicides;
a13) auxin herbicides;
a14) auxin transport inhibitors;
a15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam, methyl bromide, and endothal;

all including the agriculturally acceptable salts and the agriculturally acceptable derivatives thereof (e.g. esters, amides or N-oxides), provided those herbicides have a group that can be derivatized, preferably a carboxyl group, an amino group or a nitrogen atom that can be oxidized, more preferred a carboxyl group.

Preferred herbicides of groups a1) to a15) are the compounds listed below:
a1) from the group of the lipid biosynthesis inhibitors:
  chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate, bensulide and pinoxaden;
a2) from the group of the ALS inhibitors:
  amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan;
a3) from the group of the photosynthesis inhibitors:
  atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;
a4) from the group of the protoporphyrinogen-IX oxidase inhibitors:
  acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen, etnipromid, and bencarbazone;
a5) from the group of the bleacher herbicides:
  metflurazon, norflurazon, flufenican, diflufenican, picolinafen, beflubutamid, fluridone, fluorochloridone, flurtamone, mesotrione, sulcotrione, isoxachlortole, isoxaflutole, benzolenap, pyrazolynate, pyrazoxyfen, benzobicyclon, amitrole, clomazone, aclonifen, 4-(3-trifluoromethyl-phenoxy)-2-(4-trifluoromethylphenyl) pyrimidine, known from EP 723960, topramezone, 4-hydroxy-3-{[2-methyl-6-(trifluoromethyl)-3-pyridinyl]carbonyl}bicyclo[3.2.1]oct-3-en-2-one, known from WO 00/15615, 4-hydroxy-3-{[2-(2-methoxyethoxy)methyl-6-(trifluoro-methyl)-3-pyridinyl] carbonyl}bicylo[3.2.1]oct-3-en-2-one, known from WO 01/94339, 4-hydroxy-3-[4-(methylsulfonyl)-2-nitrobenzoyl]bicyclo[3.2.1]-oct-3-en-2-one, known from EP 338992, 2-[2-chloro-4-(methylsulfonyl)-3-[(2,2,2-trifluoroethoxy)methyl]benzoyl]-3-hydroxy-2-cyclohexen-1-one (known from DE 19846792), and pyrasulfotole;
a6) from the group of the EPSP synthase inhibitors: glyphosate;
a7) from the group of the glutamine synthase inhibitors: glufosinate and bilanaphos;

a8) from the group of the DHP synthase inhibitors: asulam;
a9) from the group of the mitose inhibitors:
  benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;
a10) from the group of the VLCFA inhibitors:
  acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;
a11) from the group of the cellulose biosynthesis inhibitors: dichlobenil, chlorthiamid, isoxaben and flupoxam;
a12) from the group of the decoupler herbicides:
  dinofenate, dinoprop, dinosam, dinoseb, dinoterb, DNOC, etinofen and medinoterb;
a13) from the group of the auxin herbicides:
  clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, clopyralid, fluoroxypyr, picloram, triclopyr, benazolin and aminopyralid;
a14) from the group of the auxin transport inhibitors: naptalam, diflufenzopyr;
a15) benzoylprop, flamprop, flamprop-M, bromobutide, chlorflurenol, cinmethylin, methyldymron, etobenzanid, fosamine, metam, pyributicarb, oxaziclomefone, dazomet, triaziflam, methyl bromide, endothal;
all of the foregoing a1) to a15) including the agriculturally acceptable salts if the herbicides have functional groups which can be ionised, in particular carboxyl groups, and, provided those herbicides have a group that can be derivatized, preferably a carboxyl group, an amino group or a nitrogen atom that can be oxidized, in particular a carboxyl group, the agriculturally acceptable derivatives of the respective herbicides, preferably esters, amides or N-oxides.

The herbicides of groups a1) to a15) are known herbicides, see the quoted literature references and, for example, The Compendium of Pesticide Common Names (http://www.hclrss.demon.co.uk/index.html); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7$^{th}$ Edition,
Weed Science Society of America, 1994; K. K. Hatzios, Herbicide Handbook, Supplement to 7$^{th}$ Edition, Weed Science Society of America, 1998, and C. D. S. Tomlin, The Pesticide Manual, 13$^{th}$ ed., BCPC, Farnham 2003.

The categorization of the herbicides according to their mode of action is based on current understanding. If a herbicide acts by more than one mode of action, this substance was assigned to only one mode of action.

If the compound (I) and/or one or more agriculturally acceptable salts thereof or the herbicides (a), are capable of forming geometrical isomers, for example E/Z isomers, it is possible to use both the pure isomers and mixtures thereof in the compositions according to the invention.

If the compound (I) and/or one or more agriculturally acceptable salts thereof or the herbicides (a) have one or more centers of chirality and, as a consequence, are present as enantiomers or diastereomers, it is possible to use both the pure enantiomers and diastereomers and their mixtures in the compositions according to the invention.

If the herbicides (a) are in form of their anionic salts, preferred cations are the same as for the anionic salts of compounds of formula (I).

If the herbicides (a) are in form of their cationic salts, preferred anions are primarily chloride, bromide, fluoride, iodide, hydrogen sulfate, methyl sulfate, sulfate, dihydrogen phosphate, hydrogen phosphate, nitrate, dicarbonate, carbonate, hexafluorosilicate, hexafluorophosphate, benzoate and the anions of $C_1$-$C_4$-alkanoic acids, preferably formate, acetate, propionate and butyrate.

According to the invention, active compounds which carry a group that can be derivatized, preferably a carboxyl group, an amino group or a nitrogen that can be oxidized, in particular a carboxyl group can, instead of the active compounds mentioned above, also be employed in the form of an agriculturally acceptable derivative, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters.

Preferred mono- and di-$C_1$-$C_6$-alkylamides are the methyl- and the dimethylamides.

Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

In binary compositions which comprise compounds of formula (I) and at least one herbicide (a), the weight ratio of the compounds of formula (I):herbicide (a) is usually in the range from 1:500 to 10:1, preferably in the range from 1:100 to 10:1, in particular in the range from 1:50 to 10:1 and particularly preferably in the range from 1:25 to 5:1.

Regarding combinations of compounds of formula (I) and herbicides (a), preference is given to those compositions of the invention which comprise compounds of formula (I) in combination with at least one, preferably exactly one, herbicidally active compound selected from the group consisting of a2) ALS inhibitors, preferably imazapyr and imazomox; a5) bleacher herbicides, preferably fluridone; a13) auxin herbicides; a14) auxin transport inhibitors, preferably diflufenzopyr; and a15) endothal.

Particularly preferred are imazomox and fluridone, especially the combinations quinclorac+imazomox, quinclorac+fluridone, quinmerac+imazomox and quinmerac+fluridone.

For application ready-to-use preparations in the form of solid formulations are generally employed. In principle, any kind of solid formulation is possible, where the particle sinks to the bottom of the water body, e.g. a pond, that is treated.

The formulations are applied, for example, in the form of granules directly to the surface of the water body that is to be treated, in a way that allows them to sink to the bottom.

Depending on the form in which the ready-to-use preparations are present, they comprise one or more solid carriers, if appropriate surfactants and if appropriate further auxiliaries which are customary for formulating crop protection products. The person skilled in the art is sufficiently familiar with the recipes for such formulations. The ready-to-use preparations may comprise auxiliaries, which are customary for formulating crop protection products.

Generally suitable for use as solid formulation in the method of the invention are granules (prills), agglomerates, pellets, microcapsules, capsules, tablets, powders and dusts, provided they are able to sink to the bottom of the water body to be treated.

Granules, pellets, microcapsules, capsules and tablets are preferred, granules are particularly preferred.

Powders and dusts can be prepared by mixing or concomitant grinding of the active compounds with a solid carrier.

Granules, e.g. granules coated by active compound(s), granules impregnated by active compound(s) and granules wherein the active compound(s) are homogenously distributed, can be prepared by binding the active compound(s) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and products of vegetable origin such as cereal meal, tree bark meal, wood meal and nutshell meal, cellulose powders, or other solid carriers.

The binding can be achieved e.g. by means of immersion, spraying or extrusion.

Pellets, microcapsules, capsules and tablets can be prepared by methods known to those skilled in the art and described, e.g. in H. Mollet, A. Gubenmann, Formulation Technology, Chapt. 6 and 12, Wiley-VCH, Weinheim 2001.

Preferred are granules, pellets, capsules and tablets, specifically granules, which are preferably applied directly in dry form, e.g. with granule applicators mounted on boats or helicopters.

Preferably, the solid formulation does not include any substantial amount of an adjuvant. Adjuvants include antifoams, thickeners, wetters, stickers, surfactants, dispersants, emulsifiers, bactericides and/or thixotropic agents.

The concentrations of the active compound(s) in the ready-to-use preparations can be varied within wide ranges. In general, the formulations comprise from 0.001 to 98% by weight, preferably 0.01 to 95% by weight, of active compound(s). The active compound(s) are preferably employed in a purity of from 90% to 100%, preferably 95% to 100% (according to NMR spectrum).

Commercially available solid formulations of quinclorac can be used for the inventive method, such as Paramount® 75DF, Facet® 75 DF and Drive® 75 DF (waterdispensable granules, available from BASF Corporation).

The compounds of formula (I) and/or one or more agriculturally acceptable salts thereof and/or herbicide(s) (a) can be formulated jointly or separately. The compounds of formula (I) and/or one or more agriculturally acceptable salts thereof and/or herbicide(s) (a) can be applied jointly or separately, simultaneously or successively, before, during or after appearance of the aquatic weeds.

The required application rate of the pure compounds (I) and/or one or more agriculturally acceptable salts thereof, optionally in combination with a further herbicide (a) without formulation auxiliary, depends on the density of the undesired vegetation, on the development stage of the plants, on the water-movement, on the climatic conditions of the location where the composition is used and on the application method. In general, the application rate is from 1 to 1000 ppb (parts per billion), preferably from 10 to 500 ppb and in particular from 250 to 500 ppb of active compound(s).

According to the invention, a solid formulation comprising a compound of formula (I) is applied to the bottom of the aqueous habitat of the bottom rooted aquatic weeds to be controlled. Application to the bottom is generally achieved by applying a solid formulation to the surface water that sinks to the bottom or floor of the body of water, before a substantial part of the active ingredient is diluted in the water.

The solid formulation is applied to the water body as either a surface or subsurface application. Surface applications are preferred. Application can be carried out by customary application techniques using, for example, granules that are generally poured directly into the aqueous habitat of the aquatic weed, and, preferably are distributed, e.g. by employing the motor blade of the boat from which the granules are applied. The density of the solid formulation, preferably granules, is chosen to ensure that the granules sink to the bottom of the aqueous habitat.

Application of the solid formulation is generally carried out from a boat, a plane, from the bank of a water body (in case of small ponds) or—in the case of shallow water—by a suitable vehicle or a person carrying the application equipment. In general, and contrary to prior applications of compounds of formula (I) to control aquatic weeds, the solid formulation is applied directly in dry and solid form to the water, i.e. without prior dilution, dispersion or dissolution in a liquid medium, in particular an aqueous medium. In this way, sedimentation of the solid formulation is improved.

The method of the invention overcomes the problem of penetrating the thermal cline, i.e. the layer between the water heated at the surface by the sunrays and the cold layer that sits below the surface.

Application of the solid formulation to the bottom of the water body brings the herbicide in contact with the soil sediment and the lower portions of the submersed aquatic weeds, such as *hydrilla* (*Hydrilla verticillata*), Mexican waterlily (*Nymphaea Mexicana*) and coontail (*Ceratophyllum demersum*). It is believed that bringing the solid formulation in contact with the soil sediment leads to a certain uptake of the active ingredient through the roots, tubers, and turions of the aquatic weeds, which can improve the efficacy.

When applying a solid formulation of a compound of formula (I) and/or an agriculturally acceptable salt thereof by the method according to this invention the aquatic weeds in general are controlled slowly, meaning the biomass of the aquatic weeds in aqueous systems, for example ponds, lakes, creeks, rivers or swamps is declining slowly and gradually. This is a big advantage compared to other herbicides for control of the aquatic weeds for example the herbicide endothall—which is also used in controlling the aquatic weeds and which exhibits very rapid, contact control of the aquatic weeds. Rapid, contact biomass reduction under high infestation levels is in general undesirable in that it for example can lead to rapid oxygen depletion in the aqueous system, which then may lead for example to significant fish mortality. Compounds providing for a slow rate of biomass reduction sufficient to maintain an average oxygen level of at least 5 mg/L in the body of water measured at a depth of about 1 meter about 30 days after application are preferred. Oxygen level testing is determined using a polarographic dissolved oxygen sensor. Several samples should be taken from several locations away from the shoreline in non-stagnant regions over a period of several hours to determine an average oxygen level.

A preferred embodiment of the invention comprises a method of using compounds of formula (I), specifically quinclorac, for controlling *hydrilla*, especially preferred *Hydrilla verticillata*.

When the inventive method (for controlling of submersed aquatic weeds) is applied in the presence of emersed aquatic weeds and/or floating aquatic weeds and/or algae, (simultaneous) controlling of emersed aquatic weeds and/or floating aquatic weeds and/or algae may (also) take place.

A further embodiment of the invention comprises allowing a herbicidally effective amount of compounds of formula (I) and/or one or more agriculturally acceptable salts thereof to act on the submersed aquatic weeds and/or its aqueous habitat containing seeds or other propagating organs of said aquatic weed in the presence of rice plants.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

Examples

Dry prills of quinclorac (commercial formulation Drive® 75 DF) were poured directly into a pond in front of the motor blade. This technique allowed the prills to be dispersed by the propellers and sinks to the bottom of the pond, penetrating the thermal layer, and placing the herbicide in contact with the pond soil sediment and the lower portions of the Mexican waterlily (*Nymphaea Mexicana*), coontail (*Ceratophyllum demersum*) and *hydrilla* (*Hydrilla verticallata*). Three ponds of coontail were treated with 100, 100 and 200 ppb. Two *hydrilla* ponds were treated with 50 and 500 ppb. One Mexican waterlily pond was treated with 200 ppb.

Complete control was measured by the end of the growing season (40 weeks after treatment) and into the following year.

Results significantly surpassed liquid injection treatments at the same or similar rates, where a liquid formulation was applied with an airboat and underwater trailing hoses.

The invention claimed is:

1. A method for controlling submersed aquatic weeds selected from the genus of *hydrilla* or from the genus of milfoil which comprises administering to a body of water a herbicidally effective amount of from 1 to 500 ppb of a solid formulation of at least one compound of formula (I)

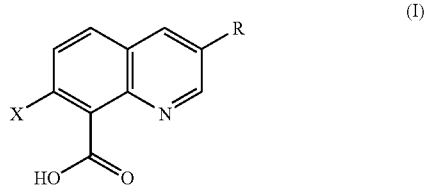

wherein
X is halogen and
R is halogen or $C_1$-$C_6$ alkyl,
and/or one or more agriculturally acceptable salts thereof, wherein the solid formulation sinks to the bottom of the aqueous habitat of the aquatic weeds to act on the submersed aquatic weeds and/or their aqueous habitat containing seeds or other propagating organs of said aquatic weeds.

2. The method according to claim 1, wherein the submersed aquatic weeds are selected from the genus of *hydrilla*.

3. The method according to claim 1, wherein the submersed aquatic weeds are selected from the genus of milfoil.

4. The method according to claim 1, wherein the compound of formula (I) is selected from quinclorac and quinmerac.

5. The method according to claim 4, wherein the compound of formula (I) is quinclorac.

6. The method according to claim 1, where the formulation is selected from granules, pellets, microcapsules, capsules, tablets, powders and dusts.

7. The method according to claim 4, where the formulation is in granular form.

8. The method according to claim 1, where the solid formulation is applied to the surface of the aqueous habitat and allowed to penetrate the thermal cline and sink to the bottom.

9. The method according to claim 1, where the solid formulation is applied in dry form.

10. The method according to claim 1, wherein the solid formulation is applied from a boat or helicopter.

11. The method according to claim 1, wherein the compound of formula (I) has a half-life in a body of water of about 50 to 60 days.

12. The method according to claim 1, wherein the aquatic weeds are tolerant and/or resistant to the herbicide fluridone.

13. The method according to claim 1, wherein a herbicidally effective amount of compounds of formula (I) and/or one or more agriculturally acceptable salts thereof are used in combination with at least one other herbicide.

14. The method according to claim 1, wherein beneficial aquatic plants are not controlled when the compound of formula (I) is administered to a body of water at 500 ppb or less.

15. The method according to claim 1, wherein substantially no amount of adjuvant is included in the solid formulation.

16. The method according to claim 1, wherein application of the compound of formula (I) to a body of water results in a slow rate of biomass reduction sufficient to maintain an average oxygen level of at least 5 mg/L in the body of water measured at a depth of about 1 meter about 30 days after application.

17. The method according to claim 5, further comprising applying imazomox in combination with quinclorac.

18. The method according to claim 4, further comprising applying imazomox in combination with quinmerac.

* * * * *